US008309113B2

(12) United States Patent
Hofmann et al.

(10) Patent No.: US 8,309,113 B2
(45) Date of Patent: Nov. 13, 2012

(54) POROUS COATING LOADED WITH A LIQUID OR A SOLID SUBSTANCE

(75) Inventors: Heinrich Hofmann, Pully (CH); Frédéric Neftel, Lausanne (CH); Laurent-Dominique Piveteau, Bussigny (CH)

(73) Assignees: Debiotech S.A., Lausanne (CH); Axis Biodental S.A., Crissier (CH)

( * ) Notice: Subject to any disclaimer, the term of this patent is extended or adjusted under 35 U.S.C. 154(b) by 336 days.

(21) Appl. No.: 11/991,751

(22) PCT Filed: Sep. 15, 2006

(86) PCT No.: PCT/IB2006/053323
§ 371 (c)(1),
(2), (4) Date: Jun. 9, 2008

(87) PCT Pub. No.: WO2007/031968
PCT Pub. Date: Mar. 22, 2007

(65) Prior Publication Data
US 2009/0098178 A1 Apr. 16, 2009

(30) Foreign Application Priority Data
Sep. 16, 2005 (EP) .................... 05108573

(51) Int. Cl.
*A61F 2/28* (2006.01)
*A61K 9/00* (2006.01)
(52) U.S. Cl. .............. 424/423; 424/93.7; 427/2.14
(58) Field of Classification Search ............... None
See application file for complete search history.

(56) References Cited

U.S. PATENT DOCUMENTS

| 6,709,379 B1 * | 3/2004 | Brandau et al. ............ 600/3 |
| 2006/0276878 A1 | 12/2006 | Owens et al. |
| 2007/0160639 A1 * | 7/2007 | Pantelidis et al. ........... 424/423 |

FOREIGN PATENT DOCUMENTS

| EP | 1 891 988 | 2/2008 |
| WO | 98/28025 | 7/1998 |
| WO | 02/43937 | 6/2002 |
| WO | 2004/043292 | 5/2004 |
| WO | 2006/063157 | 6/2006 |

OTHER PUBLICATIONS

Piveteau et al., "Evaluating mechanical adhesion of sol-gel titanium dioxide coatings containing calcium phosphate for metal implant application," Biomaterials 21 (2000) 2193-2201.*
Bartlett et al., "Highly Ordered Macroporous Gold and Platinum Films Formed by Electrochemical Deposition through Templates Assembled from Submicron Diameter Monodisperse Polystyrene Spheres," Chem. Mater. 2002, 14. 2199-2208.*
Stein et al., "Sphere templating methods for periodic porous solids," Microporous and Mesoporous Materials 44-45(2001) 227-239.*
Bartlett et al., "Highly Ordered Macroporous Gold and Platinum Films Formed by Electrochemical Deposition through Templates Assembled from Submicron Diameter Monodisperse Polystyrene Spheres," Chem. Mater. 2002, 14, 2199- 2208.*
Bartlett et al "Highly Ordered Macroporous Gold and Platinum Films Formed by Electrochemical Deposition through Templates Assembled from Submicron Diameter Monodisperse Polystyrene Spheres," Chem. Mater. 2002, 14, 2199-2208.*
Stein et al "Sphere templating methods for periodic porous solids," Microporous and Mesoporous Materials 44-45 (2001) 227-239.*
Hyodo et al., "Preparation of macroporous SnO2 films using PMMA microspheres and their sensing properties to NOx and H2", *Sensors and Actuators B, Elsevier Sequoia S.A.*, pp. 580-590, XP004867911.
Peng, "Surface-templated nanostructured films with two-dimensional ordered arrays of voids", *Angewandte Chemie*, vol. 43, No. 42, Oct. 2004, pp. 5625-5628, XP002365896.
Park et al., "A facile route to prepare high surface area mesoporous SiC from SiO2 sphere templates", *Journal of Materials Chemistry*, 14(23), pp. 3436-3439, XP002365897.
Bartlett et al., "Highly ordered macroporous gold and platinum films formed by electrochemical deposition through templates assembled from submicron diameter monodisperse polystyrene spheres", *Chemistry of Materials, American Chemical Society*, vol. 14, No. 5, May 2002, pp. 2199-2208, XP002353386.
Ko et al., "Fabrication of colloidal self-assembled monolayer (SAM) using monodisperse silica and its use as a lithographic mask", *Preparation and Characterization*, Elsevier Sequoia, NL, vol. 447-448, Jan. 2004, pp. 638-644, XP004493813.
Piveteau et al., "Evaluating mechanical adhesion of sol-gel titanium dioxide coatings containing calcium phosphate for metal implant application", *Biomaterials*, Elsevier Science Publishers BV., Barking, vol. 21, No. 21, Nov. 2000, pp. 2193-2201, XP004216035.
International Search Report for PCT/IB2006/053323 mailed Mar. 7, 2007.
Written Opinion for PCT/IB2006/053323 mailed Mar. 7, 2007.
Office Action dated Feb. 18, 2010 from U.S. Appl. No. 12/066,114.
Jiang et al. "Large scale fabrication of periodic nanostructured materials by using hexagonal non-close-packed colloidal crystals as templates," *Langmuir*, 2006, vol. 22 (9) pp. 3955-3958.
Cho et al, "Two-Dimensional, open-pored, mesoscopic titania layers using polymeric nanoparticle monolayers as a template," Advanced Materials, 2004, vol. 16, No. 20, Oct. 18, pp. 1814-1817.
Office Action dated Sep. 8, 2009 from U.S. Appl. No. 12/066,114.

* cited by examiner

*Primary Examiner* — Suzanne Ziska
(74) *Attorney, Agent, or Firm* — Nixon & Vanderhye P.C.

(57) ABSTRACT

The present invention relates to a process for manufacturing a porous coating with structures in the micro or nano-size domain characterized by the following steps:—providing a support having a surface,—depositing on the surface one mono-layer of temporary particles,—depositing a coating on the temporary particles in such a way that the thickness of the coating is less than the particle diameter,—eliminating the temporary particles and thereby obtaining a porous coating, the pores of the coating corresponding to the spaces previously occupied by the temporary particles and at least a part of the pores communicating with the external environment,—applying a coating fixation step, characterized by the fact that it furthermore comprise a filling step where the pores are at least partially filled with a liquid or solid substance. The invention also concerns a coating and an object which can be obtained with this process.

8 Claims, 8 Drawing Sheets

POROUS COATING LOADED WITH A LIQUID OR A SOLID SUBSTANCE

This application is the U.S. national phase of International Application No. PCT/IB2006/053323 filed 15 Sep. 2006 which designated the U.S. and claims priority to European Patent Application No. 05108573.6 filed 16 Sep. 2005, the entire contents of each of which are hereby incorporated by reference.

FIELD OF INVENTION

The present invention relates to porous coatings with controlled structure in the micro and nano-size domain. In particular, but not exclusively, it relates to processes for fabricating such surfaces and to objects obtained according to such processes.

BACKGROUND OF THE INVENTION

Various techniques have been employed to achieve the preparation of porous coatings using colloidal particles. They can be classified in laser techniques [Hua1, Li1], classical colloidal, or nanosphere, lithography [Ko1, Jia3, Den2, Ryb1], soft lithography [Cho2], three-dimension particle template deposition and infiltration techniques [Jia1, Par, Sch, Hyo1, Bar] or one-step deposition techniques [Kan1, Xu1]. The references between square brackets are copied below:

[Jia1] P. Jiang, "Surface-templated nanostructured films with two-dimensional ordered arrays of voids", Ange. Chem. Int. Ed. 2004, 43, 5625-5628.
[Hua] S. M. Huang, M. H. Hong, B. S. Luk'yanchuk, Y. W. Zheng, W. D. Song, Y. F. Lu, T. C. Chong, "Pulsed laser-assisted surface structuring with optical near-field ehanced effects", J. Appl. Phys. 2002, 92(5), 2495-2500.
[Ko] H.-Y. Ko, H.-W. Lee, J. Moon, "Fabrication of colloidal self-assembled monolayers (SAM) using monodisperse silica and its use as a lithographic mask", Thin Solid Films 2004, 447-448, 638-644.
[Sch] R. C. Schroden, M. Al-Daous, C. F. Blanford, A. Stein, "Optical properties of inverse opal photonic crystals", Chem. Mater. 2002, 12, 3305-3315.
[Jia2] P. Jiang, M. J. McFarland, "Wafer-scale periodic nanohole arrays templated from two-dimensional nonclose-packed colloidal crystals", J. Am. Chem. Soc. 2004, 127, 3710-3711.
[Kan] M. Kanungo, M. M. Collinson, "Fabrication of two-dimensionally ordered macroporous silica materials with controllable dimensions", Chem. Comm. 2004, 548-549.
[Li] L. P. Li, Y. F. Lu, D. W. Doerr, D. R. Alexander, J. Shi, J. C. Li, "Fabrication of hemispherical cavity arrays on silicon substrates using laser-assisted nanoimprinting of self-assembled particles", Nanotechnology 2004, 15, 333-336.
[Par] K.-H. Park, I.-K. Sung, D.-P. Kim, "A facile route to prepare high surface area mesoporous SiC from $SiO_2$ sphere templates", J. Mater. Chem. 2004, 14 3436-3439.
[Bri] E. P. Briggs, A. R. Walpole, P. R. Wilshaw, M. Karlsson, E Palsgard, "Formation of highly adherent nano-porous alumina on Ti-based substrates: a novel bone implant coating", J. Mater. Sci.: Mat. Med. 2004, 15, 1021-2029.
[Den] F. A. Denis, P. Hanarp, D. S. Sutherland, Y. F. Dufrêne, "Nanoscale chemical patterns fabricated by using colloidal lithography and self-assembled monolayers", Langmuir 2004, 20, 9335-9339.
[Cho] D.-G. Choi, S. G. Jang, H. K. Yu, S.-M. Yang, "Two-dimensional polymer nanopattern by using particle-assisted soft lithography", Chem. Mater. 2004, 16, 3410-3413.
[Ryb] J. Rybczynski, U. Ebels, M. Giersig, "Large-scale, 2D arrays of magnetic nanoparticles", Col. Surf. A: Physicochem. Eng. Aspects, 2003, 219, 1-6.
[Xu] H. Xu, W. A. Goedel, "Polymer-silica hybrid monolayers as precursors for ultrathin free-standing porous membranes", Langmuir 2002, 18(6), 2363-2367.
[Hyo1] T. Hyodo, K. Sasahara, Y. Shimizu, M. Egashira, "Preparation of macroporous $SnO2$ films using PMMA microspheres and their sensing properties to NOx and H2", Sens. Act. B 2005, 106, 580-590.
[Bar] P. N. Bartlett, J. J. Baumberg, P. R. Birkin, M. A. Ghanem, M. C. Netti, "Highly ordered macroporous gold and platinum films formed by electrochemical deposition through templates assembled from submicron diameter monodisperse polystyrene spheres", Chem. Mater. 2002, 14, 2199-2208.

GENERAL DESCRIPTION OF THE INVENTION

The present invention offers another approach for fabricating porous coatings in the micro or nano-size domain.

To this effect it relates to a process for manufacturing a porous coating with structures in the micro or nano-size domain characterized by the following steps:
providing a support having a surface,
depositing on said surface one mono-layer of temporary particles,
depositing a coating on said temporary particles in such a way that the thickness of said coating is less than the particle diameter,
eliminating said temporary particles and thereby obtaining a porous coating, the pores of said coating corresponding to the spaces previously occupied by the temporary particles and at least a part of the pores communicating with the external environment,
applying a coating fixation step,
characterized by the fact that it furthermore comprise a filling step where
said pores are at least partially filled with a liquid or solid substance.

Preferred processes according to the invention are defined in the dependent claims.

The invention also relates to a porous coating with structures in the micro or nano-size domain obtained according to above cited process, said porous coating having pores which are, at least partially, filled with a liquid or a solid substance.

Preferred porous coatings according to the invention are defined in the dependent claims.

Finally, the invention relates also an object comprising a coating as defined above.

Preferred objects according to the invention are defined in the dependent claims.

Using the present invention allows a precise control of the porosity, the chemical composition and the thickness of the coating. It also offers the advantage of producing coatings with relatively important porosities and thickness. Cavities with sizes between several tenth of nanometers and a few tenths of microns and porosities of 60% can be achieved. Thickness greater than 200 nm can be obtained allowing thereby the manufacturing of specific objects with the capacity to store a significant amount of a given substance or with a significant porosity to allow tissue ingrowth. These can be used for various applications such as, but not exclusively, drug eluting stents, bioactive or drug eluting orthopedic implants, bioactive or drug eluting dental implants.

In the present text, the term "eliminating" is used in a broad sense. It covers any commonly used terms related to an important change in the particle morphology, such as for example disintegration, dissolution or removal. For instance, but not exclusively, elimination of the temporary particles may comprise a thermal step, a chemical step, a mechanical step, an electro-mechanical or an irradiation step. In the case of a thermal, a chemical or an irradiation step, the temporary particles are either completely destroyed or only partially, e.g. the particles can be made hollow. In the case of a mechanical step, the temporary particles can be mechanically removed. In the case of an electro-mechanical step (e.g. sonication or ultrasonic vibrations), the particles can be swelling (e.g. by use of polymeric particles, such as PLGA) or disintegrated.

The term "temporary" has to be understood as "present only for a limited time during the process". Temporary particles can be viewed as templates that create the tri-dimensional structure and porosity of the coating.

The expression "mono-layer of particles" means that the particles are at the same level relatively to the surface of the support. For each mono-layer, no particle will sit on top of another.

Substrate

The substrate can be made of any type of material: metal, ceramic or polymer. Metals such as stainless steel, Nitinol, titanium, titanium alloys, or aluminum and ceramics such as zirconia, alumina, or calcium phosphate are of particular interest. Furthermore, the substrate can also be made of a layer of temporary particles.

Coating Composition

In the same way, the coating can be made of different types of materials: metals, ceramics, polymers, hydrogels or a combination of any of these materials. For example, the coating can be made of a ceramic with an organic binder. Such combination reduces the risk of crack formation at the surface.

As the porous coating may be in contact with a living body, it is preferably made of a biocompatible material. Depending on applications this can be, but not exclusively, an oxide, a phosphate, a nitride or a carbonitride. Among the oxide the following ones are preferred: tantalum oxide, aluminum oxide, zirconium oxide or titanium oxide. When using aluminum, the process may advantageously comprise a further anodisation step, which both increases the biocompatibility and further creates a nanoporous additional structure.

Particles

The diameter and the shape of the temporary particles can be chosen arbitrarily. But a preference is given for homogeneous particles in shape and size. The chemical composition of the particles is also free, but it is preferably selected in the group of polymers, starch, silica, metals or biological materials such as cells. A preference is given for polymers materials with a spherical shape and homogeneous diameter: mono-disperse polymer beads. For example, polystyrene bead may be advantageously used. They are readily available in numerous sizes and are very consistent in size. Alternatively, biocompatible polymers (e.g. PLGA or Poly Lactide Glycolide Acid type) can also be used.

When deposited on the support temporary particles can either be in contact with each other or separated by some empty space. When in contact, the contact surface size can be modified by changing the surface chemistry and surface affinity of the particles. It can be increased by using wettable particles or reduced to a point-like contact when using non-wettable particles such as Teflon.

Using hydrophilic and/or hydrophobic temporary particles allows the creation of various structures in the coating. Before the deposition of the temporary particles, the substrate is locally covered with a hydrophilic respectively a hydrophobic layer. In this way specific zones are adapted to fix temporary particles with a similar surface affinity while attachment on the other zones is prevented. In the case of a stent, it may be advantageous to only coat regions which are less subject to deformations; alternatively it may be advantageous to only coat regions which are in contact with the intima of the vessel to target the release of drug to prevent proliferation or inflammation. In the case of bone or dental implants, it may be advantageous to select regions where bone ingrowth should be favored and where it should be hindered.

Coating Deposition

Different procedures can be considered for the coating deposition. They are chosen according to the coating precursors that are used as well as to the desired properties of the coating. A few examples are given below:

A first procedure to deposit the coating onto the substrate uses a mixture of nanoparticles in a solvent such as for example water as coating precursor. The substrate is dipped into the precursor mixture and pulled out at a controlled speed. The thickness of the coating varies with the viscosity of the mixture and with the pulling speed.

Another procedure uses a sol obtained through hydroxylation and partial condensation of a metallic alkoxyde as coating precursor. Again, the precursor can be coated onto the substrate using either dip or spin coating.

In an other procedure, a slurry containing both the temporary particles and the coating precursor dissolved in, for example, water is coated onto the substrate.

In all cases the coating can be deposited in several steps or sublayers. Between the depositions of each sub-layer the solvent of the coating precursor can be partially or fully removed by, for example, a thermal treatment. This approach permits the formation of thicker, crack-free coatings. The composition of the coating precursor can also be modified between each step. This allows the creation of coatings with variable chemical composition. For example, the chemical composition of the coating can be very similar to that of the substrate at the coating/substrate interface and can be very compatible at the interface with the body.

Using nanopowders or a sol-gel approach for producing coatings offers the advantage of reducing the necessary temperature for obtaining crystalline coatings. This is particularly favorable for metallic substrates that may go through phase transitions when thermally treated and therefore lose part of their mechanical or shape memory properties.

An example of such process would be the use of Zircon nanopowder (obtained from Buhler, Uzwil, Switzerland), which enables a sintering between 1,100° C. and 1,200° C. instead of between 1,400° C. and 1,500° C. for standard Zircon powder.

Similar results are obtained with titanium sols produced from tetrabutyl ortho-titanate hydrolized with a mixture of water and nitric acid in absolute ethanol. Crystalline $TiO_2$ in an anatase phase is obtained after a thermal treatment of a few minutes in air between 600° C. and 850° C.

Particles Removal

The elimination of the temporary particles can be achieved by different methods such as for example, but not exclusively, a thermal, a chemical, a mechanical, an electro-mechanical, a photo-chemical or an irradiation step. It can also take place at different stages of the process, before and/or during and/or after the fixation step, depending on the coating requirements Fixation Any appropriate method can be used for the fixation step. Advantageously a drying step is used.

For ceramics this can be sintering where the crystalline phase is formed. For a polymer this can be a photo-chemically (by visible of UV light), a thermally or chemically induced polymerisation. For metals or for certain ceramics this can be a thermal treatment under controlled (neutral or reducing) atmosphere.

Filling of the Coating

Once created, the pores may be filled with a drug of interest, e.g. by dip-coating. The pH of the solution containing the drug can be also adjusted to change the charge present at the surface of the coating and thus facilitating the penetration of the drug into the pores. Another way to facilitate loading is to make pores out of a hydrophobic respectively hydrophilic materials and fill them with a lipophilic respectively hydrophilic solution.

Loading the implant with different drugs can be achieved by creating cavities of different sizes. The cavities are then filled with drug loading vesicles of different sizes, whereby the larger cavities are filled first with larger vesicles (i.e. large vesicles are too big to fill the smaller cavities) and smaller cavities are later filled with smaller vesicles which will fill the remaining places available (i.e. in the small cavities remaining empty). Such a technique enables to store different drugs into the coating which may have different delivery profiles in time which may depend e.g. on the release properties of the vesicles selected (such as hydrophobic or hydrophilic properties; or polymer degradation properties).

Furthermore, the cavities (pores) may be filled by any other appropriate liquid or solid substance, e.g. growth factors, bone cells, other cells, etc.

Double D&d Coating

A special type of coating covered by this invention is made by depositing two types of temporary particles of different diameters D and d. The process is similar to that presented above and can be described by a series of steps that can be conducted in any order or in parallel:

1) a support or substrate having a surface is provided
2) a first mono-layer of temporary particles with a diameter D are deposited onto the support or substrate
3) a second layer of particles with a diameter d where d is smaller than D is deposited above the mono-layer. Combined with the first mono-layer, it forms a temporary particles construction
3) a coating precursor is deposited onto the support or substrate in such a way that the upper part of the temporary particles construction is not covered by it but that larger particle of the lower mono-layer a fully covered
4) the temporary particles are eliminated releasing cavities of controlled shape and size and constituting a porous coating
5) the coating is then consolidated through a fixation step In this process, the cavities (or porosity) obtained in place of the particles of D size will be in open contact with the cavities (or porosity) obtained in place of particles of d size at the former contact points between D particles and d particles, thereby limiting the size of the exit of the D cavities, through the former d particles layer, to a limited size which is defined by either the size of the openings obtained at the contact points between the former D particles and d particles or to the maximum pore size obtained at the outside of the former d particles layer.

By changing the wettability of the particles, the size of the contact points of the pores can be modified. It can be decreased by using hydrophilic particles and increased by using hydrophobic ones.

This technique is particularly interesting for enabling an important drug loading into the large cavities produced by the large particles, while limiting the release in time of such drug though smaller pores resulting from the former smaller particles.

Object

The processes previously discussed allow the manufacturing of objects with specific and original features. These objects structurally differ from the prior art objects due to the specific processes used.

A major application for these objects is in the field of medical implants. Of particular interest are stents, orthopedic and dental implants. The porosity can be used as a drug reservoir that will release its content in a controlled way over time or it can be used to favor tissue ingrowth and therefore increase the mechanical interlocking between the implant and the living tissue.

For stents the coating can be loaded with one or several drugs. It can be a combination of the following drugs given as non-exclusive examples: an anti-proliferative agent, an anti-coagulation substance, an anti-infectious, an bacteriostatic substance.

The object can also be an orthopedic or dental implant wherein the pores may be adapted in the same manner as for the stent discussed above. In such case, the porosity obtained can either be of interest to store growth factors such as bone growth factors, increase biocompatibility or create regions where bone or cartilaginous tissue can grow and attach in a solid manner to the implant. This can also be achieved by filling the cavities with resorbable bioactive ceramics such as calcium phosphates.

The pore size may also be adapted for diffusing beads, particles or polymers containing an active substance which can be slowly released.

Alternatively the beads or particles can emit an irradiation. Advantageously, in such case, the beads or particles shall remind within the cavities.

FIGURES AND TABLES

The present invention will be more fully understood from the following figures and table:

Table 1 below summarizes different possibilities for manufacturing a porous surface according to the present invention

TABLE 1

| Colloidal mask's materials | Coating's material | Consolidation techniques | Elimination methods of the colloids: before, during or after the consolidation step |
|---|---|---|---|
| Polymer | Polymer | UV-, Thermal-Polymerisation | After - Chemical selective dissolution |
| Polymer | Metal | Thermal-Annealing, . . . | Before or after - Chemical selective dissolution<br>Before or after - UV-irradiation, oxygen plasma<br>During - Pyrolsis<br>After - Mechanical (ultrasonic, . . . ) |
| Polymer | Ceramics | Thermal-Sintering | Before - Chemical selective dissolution<br>Before - UV-irradiation, oxygen plasma<br>During - Pyrolysis |
| Metal | Polymer | UV-, Thermal-Polymerisation | After - Chemical selective dissolution |
| Metal | Ceramics | Thermal-Sintering | Before - Chemical selective dissolution |
| Ceramics | Polymer | UV-, Thermal-Polymerisation | After - Chemical selective dissolution<br>After - Mechanical (ultrasonic, . . . ) |
| Ceramics | Metal | Thermal-Annealing, . . . | Before or after - chemical selective dissolution<br>After - Mechanical (ultrasonic, . . . ) |
| Ceramics | Ceramics | Thermal-Sintering | Before or after - chemical selective dissolution |

ILLUSTRATIVE EMBODIMENTS

Example 1

Figure 1:
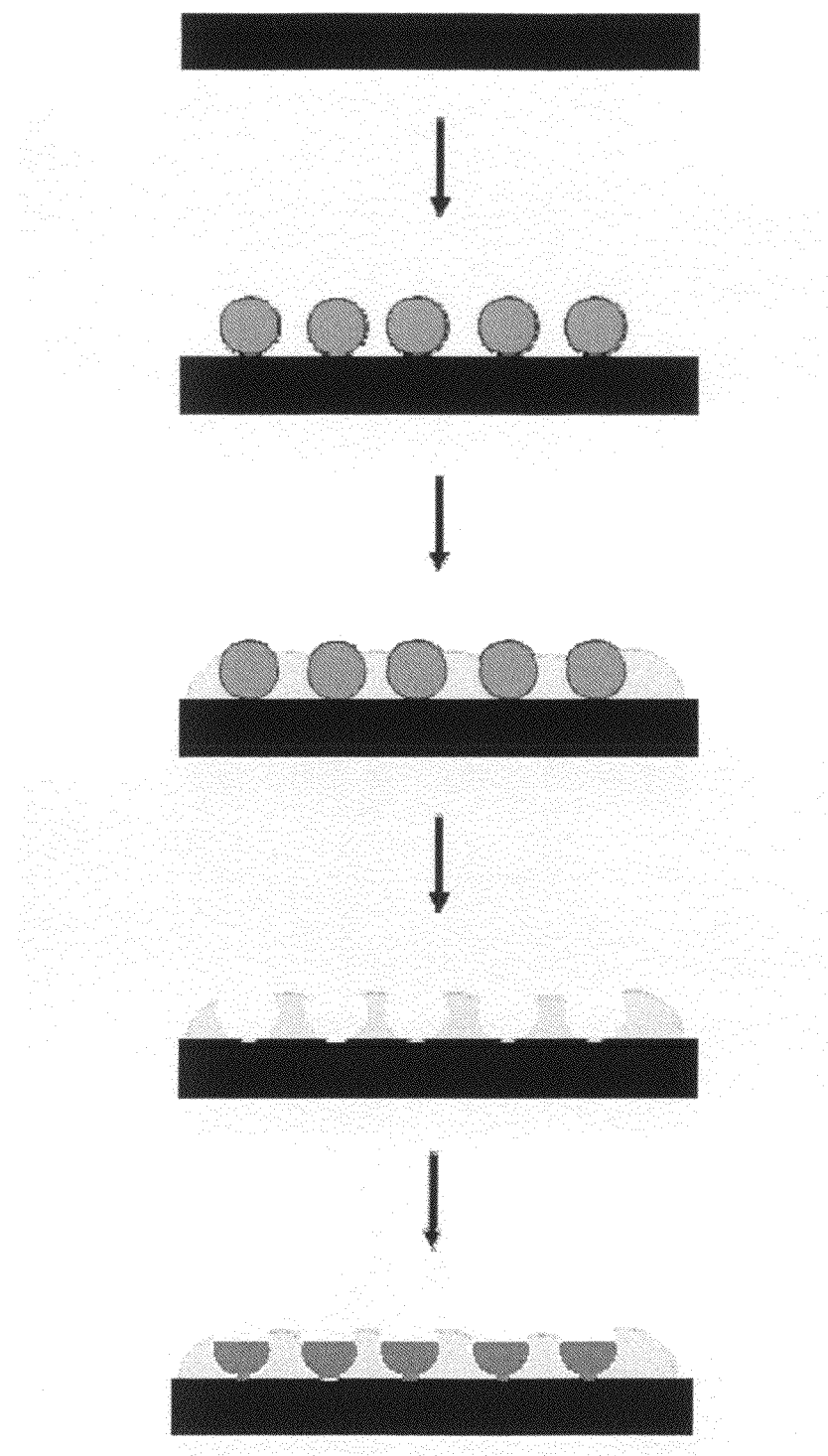
FIG. 1 is a schematic representation of a process according to the invention for manufacturing a coating with one layer of pores.
Figure 2:
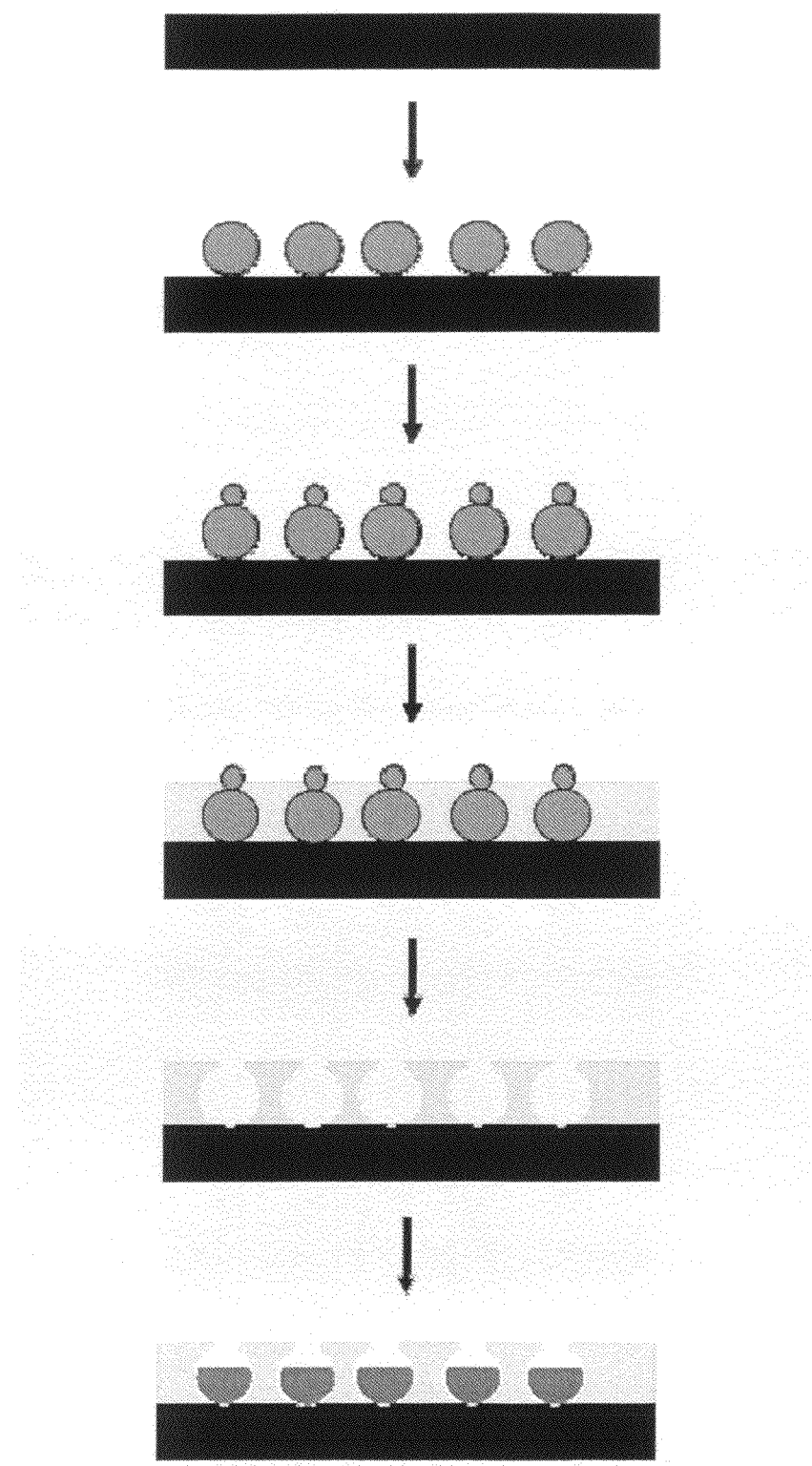
FIG. 2 is a schematic representation of a process according to the invention for manufacturing a coating with two layers of pores.
Figure 3:
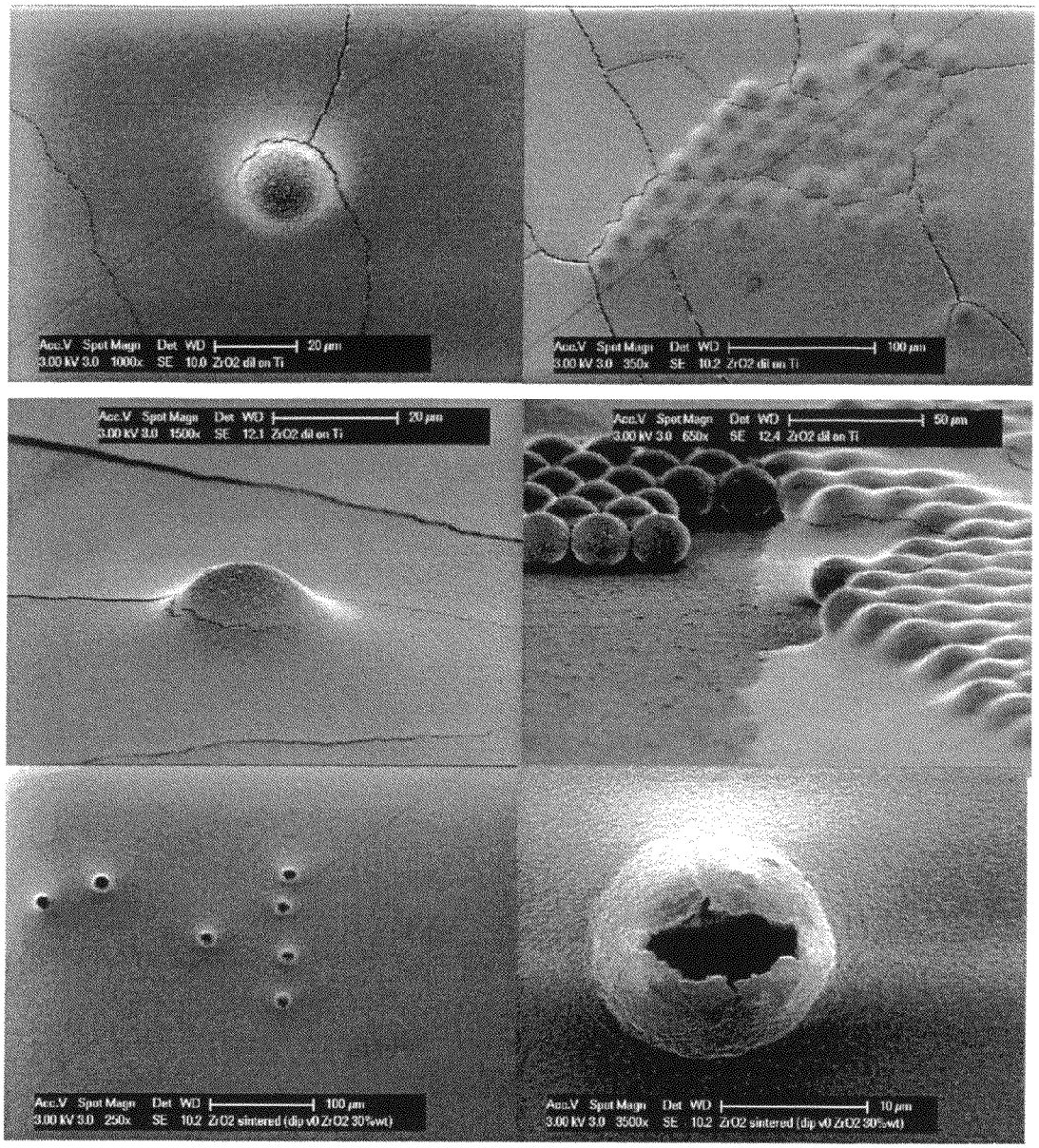
FIG. 3 shows different pictures of an embodiment of the invention. It is described at the first example in this patent.

Polystyrene particles (PS) of 4, 20 and 40 μm are used. The substrate is a zircon green body containing binding agents. The PS particles are deposited on the zircon piece by drying a droplet of a PS suspension onto the substrate. The solvent is a mixture of a low surface tension solvent, ethanol, and a surfactant, n-octanol. This is used to avoid the formation of compact ordered arrays of removable particles. Following this first step, the zircon green body is dip-coated in an aqueous suspension containing a high particle concentration (30 wt %) of $ZrO_2$ particles with either PolyVynil Alcohol (PVA) or PolyEthylene Glycol (PEG) as binders in a concentration of 5 wt %. These particles have a typical diameter of about 50 nm. Dip-coating is conducted at a removal speed between 0.03 and 10.0 mm/min. The resulting $ZrO_2$ layer is shown in FIG. 3. After the dip-coating step, sintering could take place as follows: from 20° C. to 500° C. at 1° C./min for the debonding step, then up to 1400° C. at 10° C./min and finally, from 1400° C. to 20° C. at 7° C./min.

Example 2

Figure 4:
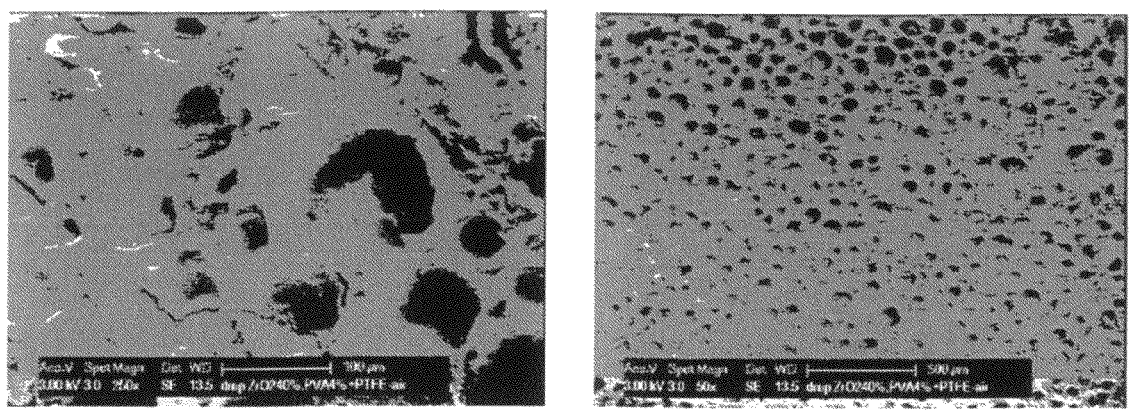
FIG. 4 shows an example of a porous surface according to the invention. It is described in the second example.
Figure 5:
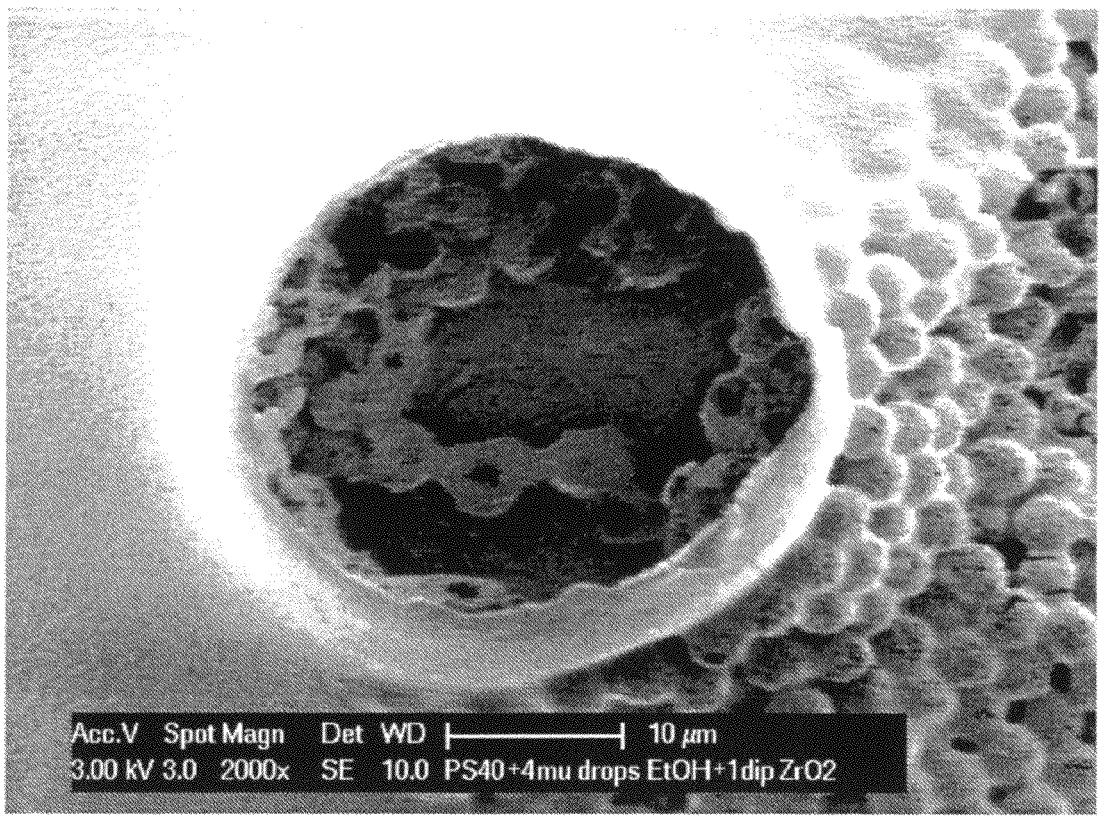
FIG. 5 shows another example with small and large pores.
Figure 6:
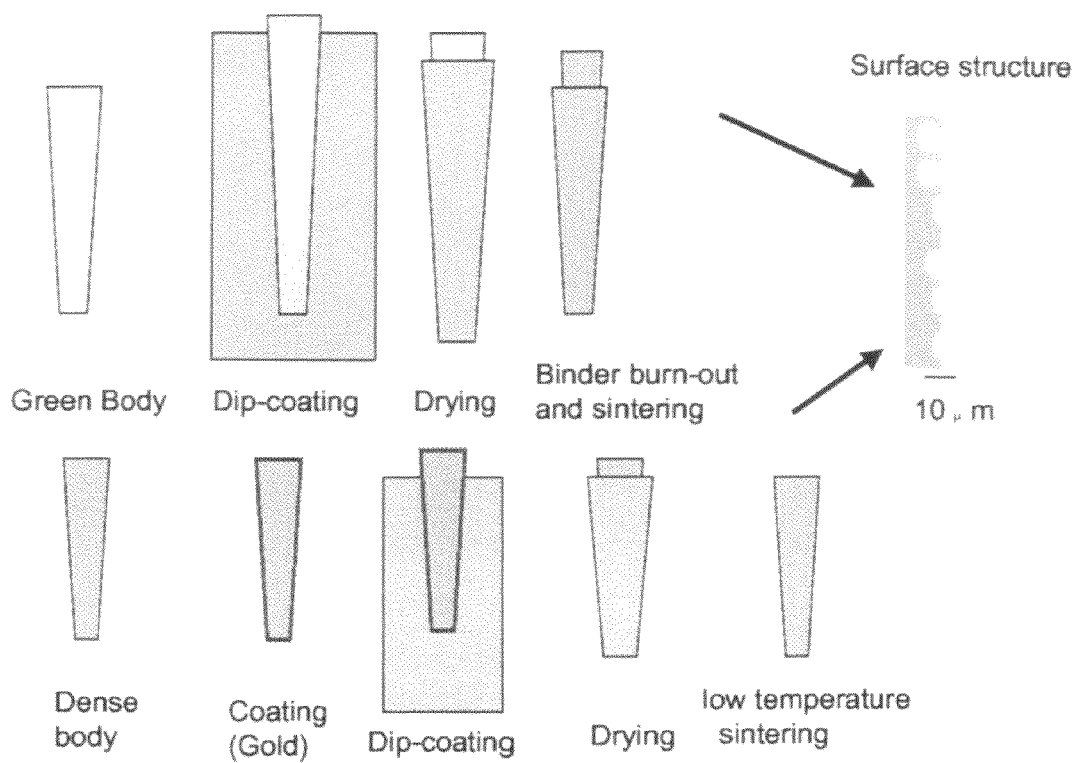
FIG. 6 is a diagram showing two different processes according to the invention.
Figure 7:
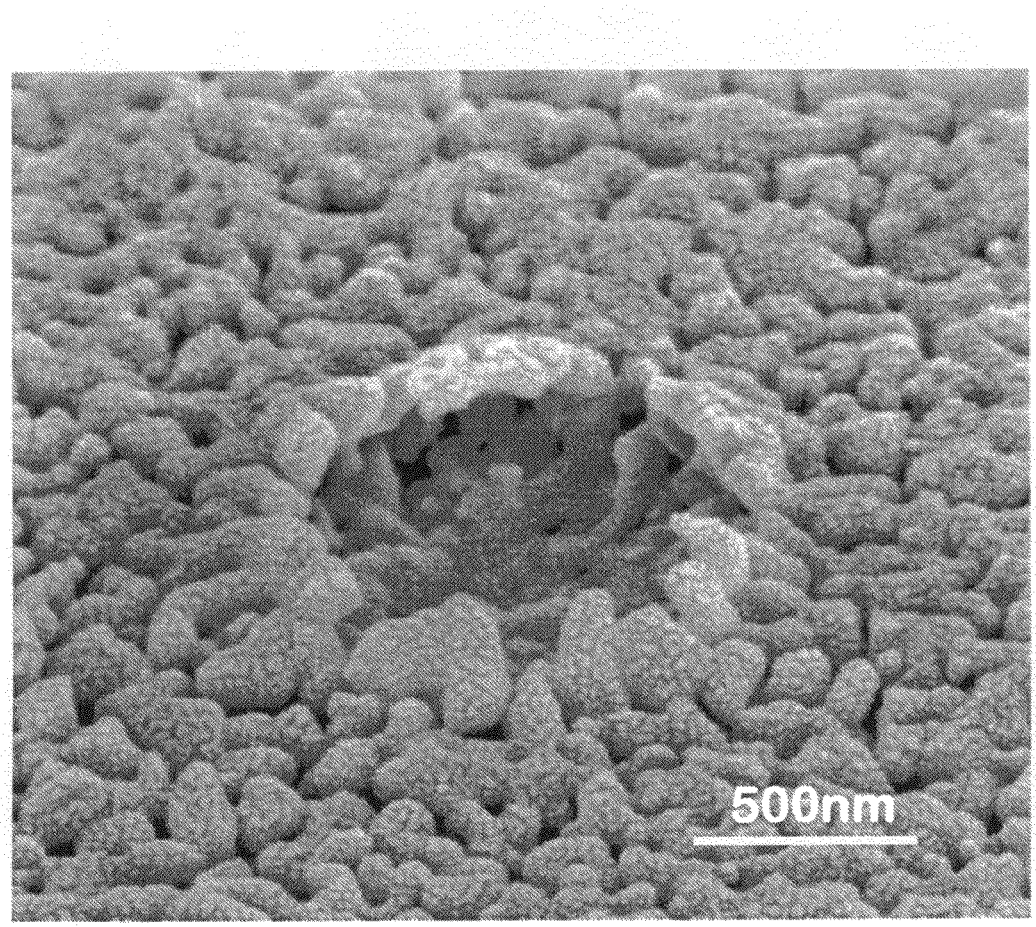
FIG. 7 shows an example of a pore according to the invention
Figure 8:
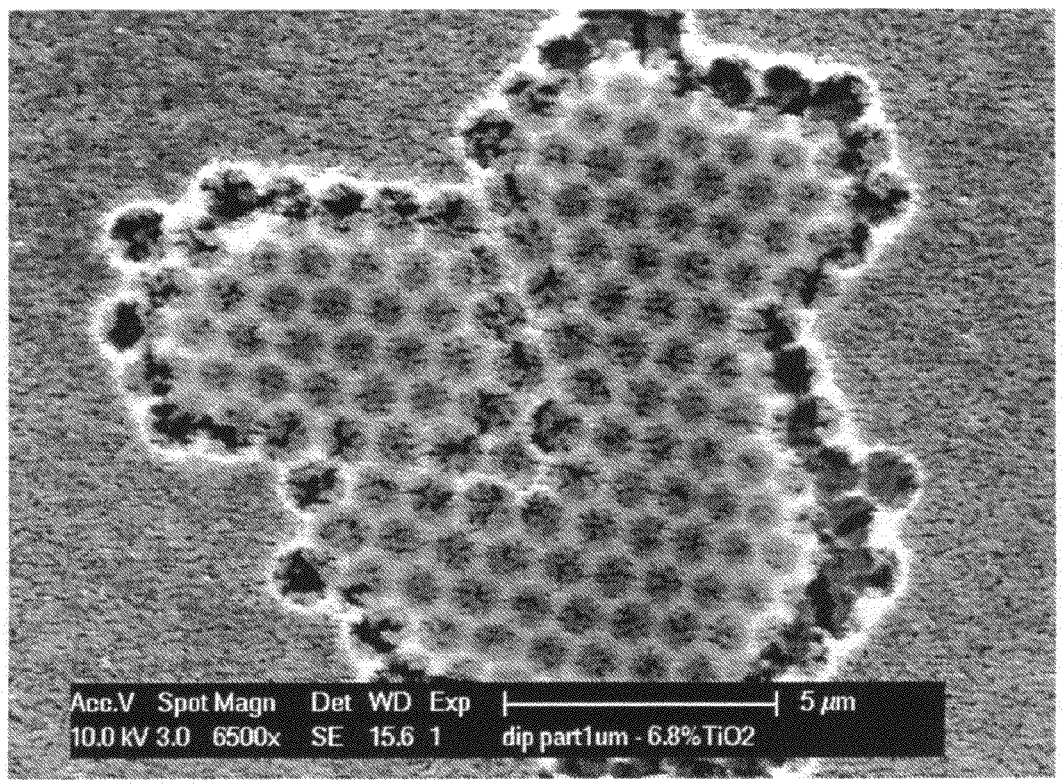
FIG. 8 shows an example of several pores according to the invention

A zircon green body containing binding agents is dip-coated in a $ZrO_2$ particles (30 wt %) solution containing binders (PolyEthylene Glycol, 5 wt %). A coating of 100 μm is deposited on top of the substrate. Dry Teflon particles are sprinkled onto the still viscous surface and then push into the coating with compressed air. The coating is then sintered following the same procedure as described in example 1. The resulting coating is shown on FIG. 4.

The invention claimed is:

1. Process for manufacturing a porous coating on a medical implant with structures in the micro- or nano-size domain consisting of the following steps:
    providing a support having a surface,
    depositing on the surface one mono-layer of temporary particles,
    depositing a coating on the temporary particles such that the thickness of the coating is less than the particle diameter,
    eliminating the temporary particles and thereby obtaining a porous coating containing pores, the pores of the porous coating corresponding to spaces previously occupied by the temporary particles and at least a part of the pores communicating with an external environment in a vertical direction from the surface,
    employing a fixation step of the porous coating,
    loading the implant by filling the pores at least partially with one or more drugs, bone growth factors, resorbable bioactive ceramics, bone cells or other cells.

2. Process according to claim 1 wherein the fixation step takes place before the particle elimination step.

3. Process according to claim 1 wherein the fixation step takes place simultaneously with the particle elimination step.

4. Process according to claim 1 wherein the fixation step takes place after the particle elimination step.

5. A medical implant comprising a porous coating obtained according to the process of claim 1.

6. A process for manufacturing a porous coating on a medical implant with structures in the micro- or nano-size domain consisting of the following steps:
    providing a support having a surface,
    depositing on the surface a first mono-layer of temporary particles with a diameter D,
    depositing on the first mono-layer a second mono layer of temporary particles with a diameter d where d is smaller than D,
    depositing a coating on the first and second mono layers of temporary particles such that an upper part of the first and second mono layers is not covered by the coating but that larger particles of the first mono-layer are fully covered,
    eliminating the temporary particles of the first and second mono layers and thereby obtaining a porous coating containing pores, the pores of the porous coating corresponding to spaces previously occupied by the temporary particles of the first and second mono layers, and wherein at least a part of the pores communicate with an external environment in a vertical direction from the surface,
    employing a porous coating fixation step,
    loading the implant by filling at least partially the pores with one or several drugs, bone growth factors, resorbable bioactive ceramics, bone cells or other cells.

7. A medical implant comprising a porous coating obtained according to the process of claim 6.

8. Process according to claim 1 wherein the thickness of the coating is more than half the particle diameter.

* * * * *